United States Patent
Kelleher-Andersson

(10) Patent No.: US 9,592,234 B2
(45) Date of Patent: *Mar. 14, 2017

(54) METHODS AND COMPOSITIONS FOR STIMULATING NEUROGENESIS AND INHIBITING NEURONAL DEGENERATION USING ISOTHIAZOLOPYRIMIDINONES

(71) Applicant: Neuronascent, Inc., Clarksville, MD (US)

(72) Inventor: Judith Kelleher-Andersson, Clarksville, MD (US)

(73) Assignee: Neuronascent, Inc., Clarksville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/751,403

(22) Filed: Jun. 26, 2015

(65) Prior Publication Data

US 2016/0022682 A1    Jan. 28, 2016

Related U.S. Application Data

(60) Continuation of application No. 14/079,489, filed on Nov. 13, 2013, now Pat. No. 9,096,613, which is a division of application No. 12/664,995, filed as application No. PCT/US2008/067742 on Jun. 20, 2008, now Pat. No. 8,609,840.

(60) Provisional application No. 60/945,524, filed on Jun. 21, 2007.

(51) Int. Cl.
| C07D 513/04 | (2006.01) |
| A61K 31/519 | (2006.01) |
| A61K 31/5377 | (2006.01) |

(52) U.S. Cl.
CPC ........ *A61K 31/519* (2013.01); *A61K 31/5377* (2013.01); *C07D 513/04* (2013.01)

(58) Field of Classification Search
CPC .......................... C07D 513/04; A61K 31/519
See application file for complete search history.

(56) References Cited

U.S. PATENT DOCUMENTS

| 3,773,919 A | 11/1973 | Boswell et al. |
| 4,089,809 A | 5/1978 | Farrior, Jr. |
| 4,233,871 A | 11/1980 | Alessi |
| 4,438,052 A | 3/1984 | Weder et al. |
| 4,438,253 A | 3/1984 | Casey et al. |
| 4,485,054 A | 11/1984 | Mezei et al. |
| 4,532,089 A | 7/1985 | MacDonald |
| 4,652,441 A | 3/1987 | Okada et al. |
| 4,897,269 A | 1/1990 | Mezei |
| 5,100,669 A | 3/1992 | Hyon et al. |
| 5,665,428 A | 9/1997 | Cha et al. |
| 5,820,880 A | 10/1998 | Alving et al. |
| 5,888,533 A | 3/1999 | Dunn |
| 6,287,588 B1 | 9/2001 | Shih et al. |
| 6,747,002 B2 | 6/2004 | Cheung et al. |
| 7,022,850 B2 | 4/2006 | Kim et al. |
| 2007/0078083 A1* | 4/2007 | Barlow ................. A61K 31/16 514/8.3 |

FOREIGN PATENT DOCUMENTS

| JP | 2007063257 A | 3/2007 |
| WO | WO-2004/098608 | 11/2004 |

OTHER PUBLICATIONS

Baraldi, et al. "Pyrazolo[4,3-d]pyrimidine Nucleosides. Synthesis and Antiviral Activity of 1-β-D-Ribofuranosyl-3-methyl-6-substituted-7H-pyrazolo[4,3-d]pyrimidin-7-ones" J. Medical Chemistry, 1984, vol. 27, p. 986-990.

Baraldi, et al. "Synthesis of 1H-Pyrazolo[4,3d]pyrimidine-7(6H)-ones and Pyrazolo-5-carboxamides and Interaction with Benzodiazepine and Adenosin $A_1$ Receptors in Rat Cerebral Cortex", Drug Research 1988, vol. 38, p. 1262-1265.

Baraldi, et al.,"Sintesi di derivati priazolici e pirazolo[4,3-d]pirimidinonici," *IL Faramaco-Edizione Scientifica*, vol. 38, Jun. 1983, pp. 369-375.

Baraldi, P.G. et al. "Synthesis of 6-substituted 3-methyl-1H-pyrazolo-[4,3-d]pyrimidine-7(6H)-ones." Inst. Chim Farm. Tossicol. Univ Ferrara. No Month Listed 1981. 2 pages.

Office Action issued by the Canadian Intellectual Property Office for Application No. 2,693,062 mailed on Jul. 15, 2014 (4 pages).

Czeh et al. "Stress-induced changes in cerebral metabolites, hippocampal volume, and cell proliferation are prevented by antidepressant treatment with tianeptine." PNAS, 98:22, 12796-12801 (Oct. 23, 2001).

European Patent Application No. 08771642 Supplementary Search Report (search completed Oct. 18, 2010) (1 page).

Forster et al. "Age-related losses of cognitive function and motor skills in mice are associated with oxidative protein damage in the brain." Proc. Natl. Acad. Sci., Neurobiology, 93: 4765-4769 (May 1996).

Kempermann et al. "Neuroplasticity in old age: sustained fivefold induction of hippocampal neurogenesis by long-term environmental enrichment." Ann. Neurol., 52: 135-143 (2002).

(Continued)

*Primary Examiner* — Robert Havlin
(74) *Attorney, Agent, or Firm* — Wilmer Cutler Pickering Hale and Dorr LLP

(57) ABSTRACT

The present invention provides methods and compositions comprising compounds useful for stimulating neurogenesis. The methods and compositions comprising compounds are also useful for inhibiting neuronal degeneration. Thus, the present invention can be used in the treatment of diseases and conditions characterized by neuronal loss and reduced neurogenesis including Alzheimer's disease, stroke, traumatic brain injury, traumatic nerve injury, and depression. This invention is useful for research products including single agents or mixtures of agents to promote, proliferate, differentiate, or maintain neurons from stem or progenitor cells.

4 Claims, 1 Drawing Sheet

(56) References Cited

OTHER PUBLICATIONS

Kubinyl, H. "Ligand-Protein Interactions and Molecular Similarity." 3D QSAR in Drug Design. Theory Methods and Applications. vol. 2-3. Springer. (1998). 800 pages.
Lee et al. "Nicotinic receptor abnormalities in the cerebellar cortex in autism." Brain, 124: 1483-1495 (2002).
Lucassen et al. "Hippocampal apoptosis in major depression is a minor event and absent from subareas at risk for glucocorticoid overexposure." American Journal of Pathology, 158:2, 453-468 (Feb. 2001).
McDonald et al. "Lifelong vitamin E intake retards age-associated decline of spatial learning ability in apoE-deficient mice." Age, 27: 5-16 (2005).
PCT/US08/067742 International Search Report mailed on Sep. 10, 2008 (2 pages).
Santarelli et al. "Requirement of hippocampal neurogenesis for the behavioral effects of antidepressants." Science, 301: 805-809 (Aug. 8, 2003).
Sumien et al. "Short-term vitamin E intake fails to improve cognitive or pyschomotor performance of aged mice." Free Radical Biology and Medicine, 36: 11, 1424-1433 (2004).
van Praag et al. "Running enhances neurogenesis, learning, and long-term potentiation in mice." PNAS, 96:23, 13247-13431 (Nov. 9, 1999).
Wang et al. "Rapid Hit to Lead Evaluation of Pyrazolo[3,4-d]pyrimidin-4-one as Selective and Orally Bioavailable mGluR1 Antagonists." Bioorganic & Medicinal Chemistry Letter, 17:4303-4307. No Month Listed 2007. 5 pages.
Wermuth. "Electronic Screening: Lead Finding from Database Mining." The Practice of Medicinal Chemistry. 2 ed. Elsevier. No Month Listed 2003. 768 pages. Chapters 9-10 provided.

\* cited by examiner

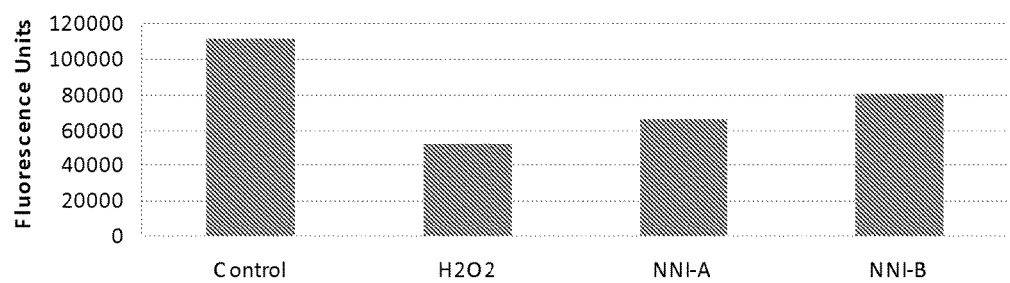

METHODS AND COMPOSITIONS FOR STIMULATING NEUROGENESIS AND INHIBITING NEURONAL DEGENERATION USING ISOTHIAZOLOPYRIMIDINONES

PRIORITY

This application is a continuation of patent application Ser. No. 14/079,489 filed Nov. 13, 2013 which is a Divisional application of patent application Ser. No. 12/664,995 filed Jun. 21, 2010, now U.S. Pat. No. 8,609,840, which claims priority to §371 patent application number PCT/US08/67742 filed Jun. 20, 2008, which claims priority to provisional application No. 60/945,524 filed Jun. 21, 2007, the disclosures of each of which are hereby incorporated by reference in their entirety.

FIELD OF INVENTION

The present invention generally relates to the field of neurology. More specifically, the present invention provides methods and compositions for stimulating neurogenesis and inhibiting neuronal degeneration.

BACKGROUND OF THE INVENTION

Alzheimer's disease is a brain disorder that gradually destroys neurons. Over 4.5 million people in America suffer from Alzheimer's, which mostly occurs in older adults. The risk of developing Alzheimer's disease approximately doubles every five years after age 65 and reaches to 50 percent by age 85. Patients afflicted with Alzheimer's disease lose their ability to learn, remember, reason, make decisions, communicate and carry out daily activities. The direct and indirect cost of caring for Alzheimer's disease patients has increased to at least $100 billion annually.

Stroke and traumatic brain injury can also cause neuronal loss and lead to cognitive decline.

The stimulation of neurogenesis may also be useful in treating depression. Depression is categorized by extreme changes in mood which may also be associated with psychoses. The association between depression, stress, and neurogenesis arose first from MRI imaging studies suggesting a reduction in right and left hippocampal volumes in major depression (Sheline et al., 1996; Bremner et al., 2000; Mervaala et al., 2000). Further research indicated that the volume loss in the brain seen in patients with depression was due to glucocorticoid-induced neuron loss specific to hippocampus (Lee et al., 2002 review; Lucassen et al., 2001; Sapolsky 2000).

Other studies further confirmed the close correlation between neurogenesis and depression. Data showed that chronic stress could cause both volume changes and reduction in neurogenesis (Czeh et al., 2001; Pham et al., 2003). On the other hand, agents that cause a reduction in neurogenesis also appear as causative agents in depression specifically glucocorticoids and depletion of serotonin (Brezun and Daszuta, 1999). Finally, research using X-rays to ablate new cells caused by fluoxetine-induced neurogenesis in mice could reverse the antidepressant behavioral activity in the novelty suppressed feeding paradigm (Santerelli et al., 2003).

One challenge for using neurogenesis to treat Alzheimer's disease or depression is that nascent neurons must still survive long enough to produce functional neurons. There exists a need for a neurogenic agent that promotes the proliferation of a neuronal precursor and that causes the differentiation and survival of the neurons.

SUMMARY OF THE INVENTION

The present invention provides methods and compositions comprising compounds useful for stimulating neurogenesis.

The methods and compositions of the present invention are particularly useful in the treatment of neurodegenerative disease like Alzheimer's disease and neuropsychiatric conditions such as depression. The methods and compositions are useful for the manufacture of research products either as one composition or as a mixture of compositions. The methods and compositions comprising compounds are also useful for inhibiting neuronal degeneration. Thus, the present invention finds particular utility in the treatment of diseases and conditions characterized by neuronal loss including, but not limited to, Alzheimer's disease, stroke, traumatic brain injury, traumatic nerve injury and depression. Disclosed herein are the compounds, methods for making the compounds, compositions comprising the compounds, and methods for using the compounds.

In one aspect, the present invention provides compositions comprising compounds useful for stimulating neurogenesis and/or inhibiting neuronal degeneration. In a one aspect, a composition may comprise a compound having the structure:

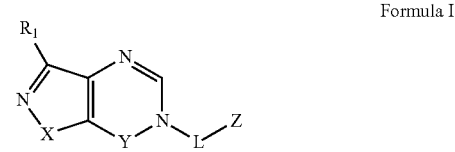

Formula I wherein $R_1$ is hydrogen, alkyl, branched alkyl, aryl, aralkyl, benzyl, napthyl, cycloalkyl of 1 to 12 carbon atoms, or a heterocycle, when $R_1$ is not hydrogen it can be optionally substituted with H, OH, alkyl, alkoxy, halogen, $-CF_3$, $-R_2$, $-OR_2$, $-SR_2$, $-N(R_2)_2$, $-CN$, $-NO_2$, $-NC(O)R_2$, $-C(O)R_2$, $-C(O)N(R_2)_2$, $-S(O)_2R_2$, $-S(O)_2NR_2$, $-S(O)R_2$, $-C(O)R_2$, $-C(O)OR_2$, or $-C(O)N(R_2)_2$ wherein each $R_2$ is independently H, alkyl, alkenyl, alkynyl, aryl, heterocycle, protecting group or prodrug moiety;

L is $[CH_2]_{2-6}$, $-CH_2-(C=O)-CH_2-$,

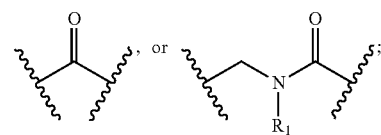

X is S, $SO_2$, O, or NH;

Y is

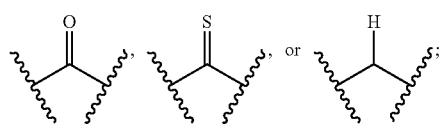

Z is

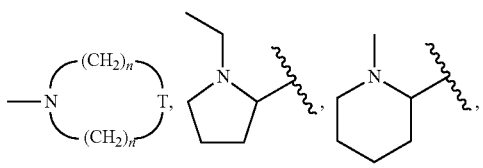

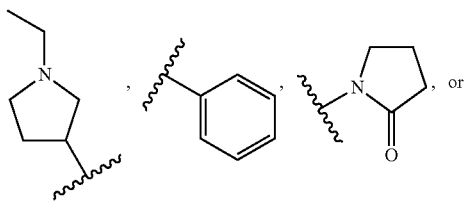

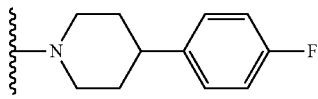

each optionally substituted with H, OH, alkyl, alkoxy, halogen, or —CF$_3$;
T is O, S, or NR$_1$;
n is 2 or 3;
wherein each R$_1$ is independent and may be the same as each other or preferably different.

In another aspect, the present invention is further directed to methods and compositions comprising compounds that have utility in the treatment of any diseases associated with neuron loss. More specifically, the present invention further provides methods for stimulating neurogenesis and/or inhibiting neuronal degeneration in a mammal. In another aspect, the method may comprise administering to a mammal a composition comprising a compound described herein. The composition comprising a compound described herein may be administered in an amount effective to stimulate neurogenesis and/or inhibit neuronal degeneration in the mammal.

In a further aspect, a method for treating a mammal afflicted with a neurodegenerative disease or condition may comprise administering an effective amount of a composition comprising a compound described herein to the mammal.

In a further aspect, a method for treating a mammal afflicted with a neuropsychiatric disease or condition may comprise administering an effective amount of a composition comprising a compound described herein to the mammal. In another aspect, the mammal is a human.

In another aspect, the human is a patient suffering from a condition selected from the neurodegenerative disease, brain injury, nerve injury, psychiatric disorders and aging.

In yet another aspect, the present invention also comprises pharmaceutical compositions comprising the compounds disclosed herein. Routes of administration and dosages of effective amounts of the pharmaceutical compositions comprising the compounds are also disclosed. The compounds of the present invention can be administered in combination with other pharmaceutical agents in a variety of protocols for effective treatment of disease.

The invention includes methods for the administration of pharmaceutical compositions comprising the compounds disclosed herein or a number of compounds together, including the use of said compounds in conjunction with other drugs and/or cell therapies to promote neurogenesis and/or neuroprotection. The present invention includes methods of administration and compositions comprising prodrug forms of the active ingredients and their transition forms.

The invention additionally includes kits comprising the compounds and compositions of the invention, as a means to provide standardized reagents and medicaments, as required by current clinical practice, as known in the art. The kits of the invention include testing and screening kits and methods, to enable practitioners to measure levels of the active ingredients in bodily fluids. The kits of the invention also include research-grade reagents and kits available for use and purchase by research entities.

DESCRIPTION OF THE FIGURE

FIG. 1 depicts the ability of NNI-A (Formula X) and NNI-B (Formula XI) inhibit neurodegeneration by hydrogen peroxide.

DETAILED DESCRIPTION OF THE INVENTION

It is understood that the present invention is not limited to the particular methodologies, assays, etc. described herein, as these may vary. It is also to be understood that the terminology used herein is used for the purpose of describing exemplary aspects of the invention, and is not intended to limit the scope of the present invention.

Unless defined otherwise, all technical and scientific terms used herein have the same meanings as commonly understood by one of ordinary skill in the art to which this invention belongs. Preferred methods and compositions are described, although any methods and compositions similar or equivalent to those described herein can be used in the practice or testing of the present invention.

I. Definitions

As used herein, the term "compound" refers to all of the iterations of the structure and formula disclosed herein and also includes a reference to a physiologically acceptable salt thereof. Examples of physiologically acceptable salts of the compounds of the present invention include salts derived from an appropriate base, such as an alkali metal, such as sodium, and alkaline earth, such as magnesium, ammonium and NX$_4^+$ (wherein X is C$_1$-C$_4$ alkyl). Physiologically acceptable salts of a hydrogen atom or an amino group may include, but are not limited to, salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of a hydroxy group include, but are not limited to, the anion of the compound in combination with a suitable cation such as $Na^+$ and $NX_4^+$ (wherein X is independently selected from H or a $C_1$-$C_4$ alkyl group).

For therapeutic use, salts of the compounds of the present invention will be physiologically acceptable, i.e., the salts will be derived from a physiologically acceptable acid or base. Salts of acids or bases, however, which are not physiologically acceptable, may also find use in the preparation or purification of a physiologically acceptable compound. Thus, all salts, whether or not derived from a physiologically acceptable acid or base, are within the scope of the present invention. Also included within this invention are pharmaceutically acceptable solvates and hydrates of the compounds.

"Alkyl" is $C_1$-$C_{18}$ hydrocarbon containing normal, secondary, tertiary or cyclic carbon atoms.

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to, ethylene or vinyl (—CH═CH$_2$), allyl (—CH$_2$CH═CH$_2$), cyclopentenyl (—C$_5$H$_7$), and 5-hexenyl (—CH$_2$CH$_2$CH$_2$CH$_2$CH═CH$_2$).

"Alkynyl" is $C_2$-$C_{18}$ hydrocarbon containing normal, secondary, tertiary or cyclic carbon atoms with at least one site of unsaturation, i.e., a carbon-carbon, sp triple bond. Examples include, but are not limited to, acetylenic (—C≡CH) and propargyl (—CH$_2$C≡CH).

The terms "alkylene" and "alkyldiyl" each refer to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like. "Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene, i.e., double carbon-carbon bond moiety. Typical alkenylene radicals include, but are not limited to, 1,2-ethylene (—CH═CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne, i.e., triple carbon-carbon bond moiety. Typical alkynylene radicals include, but are not limited to, acetylene (—C≡C—), propargyl (—CH$_2$C≡C—), and 4-pentynyl (—CH$_2$CH$_2$CH$_2$C≡CH—).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Heteroaryl" means a monovalent aromatic radical of one or more carbon atoms and one or more atoms selected from N, O, S, or P, derived by the removal of one hydrogen atom from a single atom of a parent aromatic ring system. Heteroaryl groups may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). Heteroaryl bicycles have 7 to 10 ring atoms (6 to 9 carbon atoms and 1 to 2 heteroatoms selected from N, O, and S) arranged as a bicyclo[4,5], [5,5], [5,6], or [6,6] system; or 9 to 10 ring atoms (8 to 9 carbon atoms and 1 to 2 hetero atoms selected from N and S) arranged as a bicyclo[5,6] or [6,6] system. The heteroaryl group may be bonded to the drug scaffold through a carbon, nitrogen, sulfur, phosphorus or other atom by a stable covalent bond. Heteroaryl groups include pyridyl, dihydropyridyl isomers, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl.

"Arylalkyl" refers to an acyclic alkyl radical in which one of the hydrogen atoms bonded to a carbon atom, typically a terminal or $sp^a$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

Substituted substituents such as "substituted alkyl," "substituted aryl," "substituted heteroaryl," and "substituted arylalkyl" mean alkyl, aryl, and arylalkyl respectively, in which one or more hydrogen atoms are each independently replaced with a substituent. Typical substituents include, but are not limited to, —X, —R, —O$^-$, —OR, —SR, —S$^-$, —NR$_2$, —NR$_3$, ═NR, —CX3, —CN, —OCN, —SCN, —N═C═O, —NCS, —NO, —NO$_2$, ═N$_2$, —N$_3$, NC(═O)R, —C(═O)R, —C(═O)NRR—S(═O)$_2$O$^-$, —S(═O)$_2$OH, —S(═O)$_2$R, —OS(═O)$_2$OR, —S(═O)$_2$NR, —S(═O)R, —OP(═O)O$_2$RR, —P(═O)O$_2$RR—P(═O)(O$^-$)$_2$, —P(═O)(OH)$_2$, —C(═O)R, —C(═O)X, —C(S)R, —C(O)OR, —C(O)O$^-$, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, protecting group or prodrug moiety. Alkylene, alkenylene, and alkynylene groups may also be similarly substituted.

"Halogens" includes F, Cl, Br or I and is used interchangeably with the word "halo."

"Heterocycle" means a saturated, unsaturated or aromatic ring system including at least one N, O, S, or P. Heterocycle thus includes heteroaryl groups. Heterocycle as used herein includes, but is not limited to heterocycles described in PAQUETTE, PRINCIPLES OF MODERN HETEROCYCLIC CHEMISTRY (W. A. Benjamin, New York, 1968), particularly Chapters 1, 3, 4, 6, 7, and 9; THE CHEMISTRY OF HETEROCYCLIC COMPOUNDS, A SERIES OF MONOGRAPHS (John Wiley & Sons, New York, 1950 to present), in particular Volumes 13, 14, 16, 19, and 28; KATRITZKY ET AL., COMPREHENSIVE HETEROCYCLIC CHEMISTRY (Pergamon Press, 1996); and 82 J. AM. CHEM. SOC. 5566 (1960).

Heterocycles include, but are not limited to pyridyl, dihydroypyridyl, tetrahydropyridyl(piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

Carbon bonded heterocycles include but are not limited to those that are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

Nitrogen bonded heterocycles include but are not limited to those that are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" means a saturated, unsaturated or aromatic ring system having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system. Monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. Carbocycle thus includes aryl groups.

As used herein, the term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow MCGRAW-HILL DICTIONARY OF CHEMICAL TERMS (S. P. Parker, Ed., McGraw-Hill Book Company, New York, 1984); and ELIEL, E. AND WILEN, S., STEREOCHEMISTRY OF ORGANIC COMPOUNDS (John Wiley & Sons, Inc., New York, 1994). Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The terms "treatment," "treating," "treat," "therapy," "therapeutic," and the like are used herein to refer generally to obtaining a desired pharmacological and/or physiological effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, and includes: (a) preventing the disease or symptom from occurring in a subject which may be predisposed to the disease or symptom, but has not yet been diagnosed as having it; (b) inhibiting the disease symptom, i.e., arresting its development; or (c) relieving the disease symptom, i.e., causing regression of the disease or symptom.

The term "pharmaceutically acceptable carrier," as used herein, refers to any and all solvents, dispersion media, coatings, antibacterial and antifungal agent, isotonic and absorption delaying agents for pharmaceutical active substances as are well known in the art. Except insofar as any conventional media or agent is incompatible with the compound, its use in the therapeutic compositions is contemplated. Supplementary compounds can also be incorporated into the compositions.

As used herein, the term "excipient" refers to the additives used to convert an active compound into a form suitable for its intended purpose. For compositions of the present invention suitable for administration to a human, the term "excipient" includes those excipients described in the HANDBOOK OF PHARMACEUTICAL EXCIPIENTS, American Pharmaceutical Association, 2nd Ed. (1994), which is herein incorporated in its entirety. The term "excipients" is meant to include fillers, binders, disintegrating agents, lubricants, solvents, suspending agents, dyes, extenders, surfactants, auxiliaries and the like. Liquid excipients can be selected from various oils, including those of petroleum, animal, vegetable or synthetic origin, such as, peanut oil, soybean oil, mineral oil, sesame oil, hydrogenated vegetable oil, cottonseed oil, groundnut oils, corn oil, germ oil, olive oil, or castor oil, and so forth.

Suitable excipients also include, but are not limited to, fillers such as saccharides, lactose, fructose, sucrose, inositol, mannitol or sorbitol, xylitol, trehalose, cellulose preparations and/or calcium phosphates, tricalcium phosphate or calcium hydrogen phosphate, as well as starch paste, using modified starch, maize starch, wheat starch, rice starch, potato starch, gelatin, tragacanth, ethoxylated isostearyl alcohols, polyoxyethylene sorbitol and sorbitan esters, microcrystalline cellulose, hydroxypropyl cellulose, methyl cellulose, hydroxypropyl methyl cellulose, aluminum metahydroxide, bentonite, sodium carboxymethylcellulose, croscarmellose sodium, crospovidone and sodium starch glycolate, and/or polyvinyl pyrrolidine and mixtures thereof. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries include, silica, stearic acid or salts thereof, such as, magnesium stearate, sodium stearyl fumarate, or calcium stearate.

The expression "therapeutically effective amount" refers to an amount of a compound disclosed herein, that is effective for preventing, ameliorating, treating or delaying the onset of a disease or condition.

The pharmaceutical compositions of the inventions can be administered to any animal that can experience the beneficial effects of the compounds of the invention. Such animals include humans and non-humans such as primates, pets and farm animals.

II. Description of the Compounds

In one aspect, the present invention includes compositions comprising a compound having the structure:

Formula I

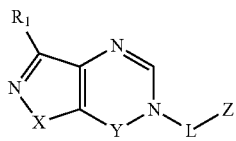

wherein $R_1$ is hydrogen, alkyl, branched alkyl, aryl, aralalkyl, benzyl, napthyl, cycloalkyl of 1 to 12 carbon atoms, or a heterocycle, when $R_1$ is not hydrogen it can be optionally substituted with H, OH, alkyl, alkoxy, halogen, —$CF_3$, —$R_2$, —$OR_2$, —$SR_2$, —$N(R_2)_2$, —CN, —$NO_2$, —NC(O) $R_2$, —C(O) $R_2$, —C(O)N($R_2$)$_2$, —S(O)$_2R_2$, —S(O)$_2$N$R_2$, —S(O)$R_2$, —C(O)$R_2$, —C(O)O$R_2$, or —C(O)N($R_2$)$_2$ wherein each $R_2$ is independently H, alkyl, alkenyl, alkynyl, aryl, heterocycle, protecting group or prodrug moiety;

L is [$CH_2$]$_{2-6}$, —$CH_2$—(C=O)—$CH_2$—,

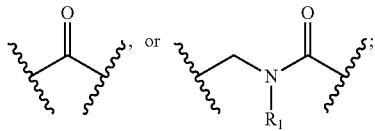

X is S, $SO_2$, O, or NH;
Y is

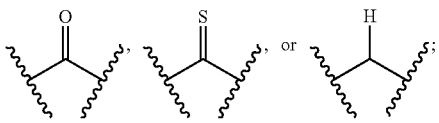

Z is

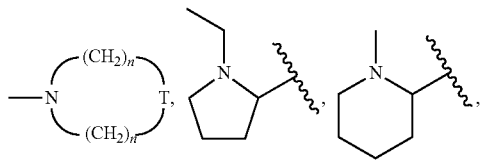

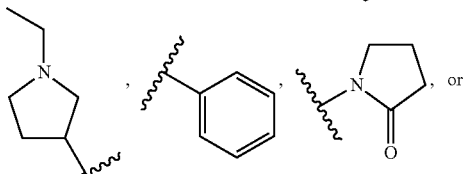

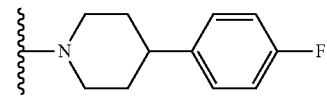

each optionally substituted with H, OH, alkyl, alkoxy, halogen, or —$CF_3$;

T is O, S, or $NR_1$;

n is 2 or 3;

wherein each $R_1$ is independent and may be the same as each other or preferably different.

Additional aspects of the invention include compounds of the following formulas and compositions comprising said compounds:

TABLE 1

| STRUCTURE | NAME |
|---|---|
| 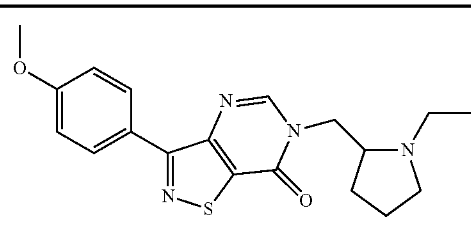 | 3-(4-Methoxyphenyl)-6-[(1-ethylpyrrolidin-2-yl)methyl]-isothiazolo[4,5-d]pyrimidin-7(6H)-one |

Formula II

TABLE 1-continued

| STRUCTURE | NAME |
|---|---|
| Formula III | 3-(4-Methoxyphenyl)-6-[3-(4-morpholinyl)propyl]-isothiazolo[4,5-d]pyrimidin-7-(6H)-one |
| Formula IV | 3-(4-chlorophenyl)-6-(3-phenylpropyl)-isothiazolo[4,5-d]pyrimidin-7(6H)-one |
| Formula V | 3-(4-Methoxyphenyl)-6-[3-(2-oxopyrrolidin-1-yl)propyl]-isothiazolo[4,5-d]pyrimidin-7(6H)-one |
| Formula VI | 3-(4-Chlorophenyl)-6-[3-(4-morpholinyl)propyl]-isothiazolo[4,5-d]pyrimidin-7(6H)-one |
| Formula VII | 3-(2-Fluoro-4-methoxyphenyl)-6-[3-(4-morpholinyl)propyl]-isothiazolo[4,5-d]pyrimidin-7(6H)-one |
| Formula VIII | 3-(4-methoxyphenyl)-isothiazolo[4,5-d]-pyrimidin-7(6H)-on-6-yl-methylamino, morpholinyl urea |

TABLE 1-continued

| STRUCTURE | NAME |
|---|---|
| Formula IX | 3-(4-methoxyphenyl)-isothiazolo[4,5-d]pyrimidin-7(6H)-on-6-yl, 4-[(4-fluorophenyl)piperidinyl] urea |
| Formula X | 6-((1-ethylpyrrolidin-2-yl)methyl)-3-(4-methoxyphenyl)isothiazolo[4,5-d]pyrimidin-7(6H)-one |
| Formula XI | 6-((1-ethylpyrrolidin-2-yl)methyl)-3-(4-fluorophenyl)isothiazolo[4,5-d]pyrimidin-7(6H)-one |
| Formula XII | 3-(4-methoxyphenyl)-6-((1-methylpiperidin-2-yl)methyl)isothiazolo[4,5-d]pyrimidin-7(6H)-one |

Finally, the general structure of the compounds of the present invention may encompass all states of saturation of the substituents shown, such as all ene, diene, triene, and yne derivatives of any substituent. The general structures also encompass all conformational isomers, regioisomers, and stereoisomers that may arise from a particular set of substituents. The general structures also encompass all enantiomers, diastereomers, and other optical isomers whether in enantiomeric or racemic forms, or mixtures of stereoisomers.

III. Compositions Comprising Compounds of the Invention

The present invention also comprises pharmaceutical compositions comprising the compounds disclosed herein. Routes of administration and dosages of effective amounts of the pharmaceutical compositions comprising the compounds are also disclosed. The compounds of the present invention can be administered in combination with other pharmaceutical agents in a variety of protocols for effective treatment of disease.

The pharmaceutical compositions of the inventions can be administered to any animal that can experience the beneficial effects of the compounds of the invention. Such animals include humans and non-humans such as pets and farm animals.

The pharmaceutical compositions of the present invention are administered to a subject in a manner known in the art. The dosage administered will be dependent upon the age, health, and weight of the recipient, kind of concurrent treatment, if any, frequency of treatment, and the nature of the effect desired.

In addition to the compounds disclosed herein, the pharmaceutical compositions of the present invention may further comprise at least one of any suitable auxiliaries including, but not limited to, diluents, binders, stabilizers, buffers, salts, lipophilic solvents, preservatives, adjuvants or the like. Pharmaceutically acceptable auxiliaries are preferred. Examples and methods of preparing such sterile solutions are well known in the art and can be found in well known texts such as, but not limited to, REMINGTON'S PHARMACEUTICAL SCIENCES (Gennaro, Ed., 18th Edition, Mack Publishing Co. (1990)). Pharmaceutically acceptable carriers can be routinely selected that are suitable for the mode of administration, solubility and/or stability of the compound.

Pharmaceutical excipients and additives useful in the present invention can also include, but are not limited to, proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination in ranges of 1-99.99% by weight or volume. Exemplary protein excipients include serum albumin such as human serum albumin (HSA), recombinant human albumin (rHA), gelatin, casein, and the like. Representative amino acid components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like.

Carbohydrate excipients suitable for use in the present invention include monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), myoinositol and the like.

The composition further can contain, but is not limited to pharmaceutically acceptable carriers such as coloring agents, emulsifying agents, suspending agents, ethanol, EDTA, citrate buffer, flavoring, and water.

The composition of the invention also can contain the preservatives methylparaben (also known as 4-hydroxybenzoic acid methyl ester; methyl p-hydroxybenzoate; or METHYL CHEMOSEPT), ethylparaben (also known as 4-hydroxybenzoic acid ethyl ester; ethyl p-hydroxybenzoate; or ETHYL PARASEPT), propylparaben (also known as 4-hydroxybenzoic acid propyl ester; propyl p-hydroxybenzoate; NIPASOL; or PROPYL CHEMOSEPT) and/or butylparaben (also known as 4-hydroxybenzoic acid propyl ester; propyl p-hydroxybenzoate; or BUTYL CHEMOSEPT). In some aspects, the composition contains methylparaben and/or propylparaben.

Emulsifiers of the invention include, but are not limited to ethyl alcohol, isopropyl alcohol, ethyl carbonate, ethyl acetate, benzyl alcohol, benzyl benzoate, propylene glycol, 1,3-butylene glycol, dimethyl formamide, oils, glycerol, tetrahydrofurfuryl alcohol, polyethylene glycols and fatty acid esters of sorbitan, and mixtures thereof.

The pharmaceutical compositions comprising the compounds of the present invention can also include a buffer or a pH adjusting agent. Typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers.

Additionally, the pharmaceutical compositions of the invention can include polymeric excipients/additives such as polyvinylpyrrolidones, ficolls (a polymeric sugar), dextrates (e.g., cyclodextrins, such as 2-hydroxypropyl-.beta.-cyclodextrin), polyethylene glycols, flavoring agents, anti-microbial agents, sweeteners, antioxidants, anti-static agents, surfactants (e.g., polysorbates such as "TWEEN 20" and "TWEEN 80"), lipids (e.g., phospholipids, fatty acids), steroids (e.g., cholesterol), and chelating agents (e.g., EDTA or EGTA). These and additional known pharmaceutical excipients and/or additives suitable for use in the present invention are known in the art, e.g., as listed in REMINGTON: THE SCIENCE & PRACTICE OF PHARMACY ($19^{th}$ ed., Williams & Williams (1995)) and PHYSICIAN'S DESK REFERENCE ($52^{nd}$ ed., Medical Economics (1998)), the disclosures of which are expressly entirely incorporated herein by reference.

The present invention provides stable pharmaceutical compositions as well as preserved solutions and compositions containing a preservative, as well as multi-use preserved compositions suitable for pharmaceutical or veterinary use, comprising at least one compound disclosed herein in a pharmaceutically acceptable composition. Pharmaceutical compositions in accordance with the present invention may optionally contain at least one known preservative. Preservatives include, but are not limited to, phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein. Non-limiting examples include, no preservative, 0.1-2% m-cresol, 0.1-3% benzyl alcohol, 0.001-0.5% thimerosal, 0.001-2.0% pheno, 0.0005-1.0% alkylparaben(s), and the like.

Other excipients, e.g., isotonicity agents, buffers, antioxidants, preservative enhancers, can be optionally added to the diluent. An isotonicity agent such as glycerin, is commonly used at known concentrations. A physiologically tolerated buffer is preferably added to provide improved pH control. The pharmaceutical compositions can cover a wide range of pHs, such as from about pH 4 to about pH 10, specifically, a range from about pH 5 to about pH 9, and more specifically, a range of about 6.0 to about 8.0. In one aspect, the formulations of the present invention have pH between about 6.8 and about 7.8. Suitable buffers include phosphate buffers, sodium phosphate and phosphate buffered saline (PBS).

Other additives, such as a pharmaceutically acceptable solubilizers like Tween 20 (polyoxyethylene (20) sorbitan monolaurate), TWEEN 40 (polyoxyethylene (20) sorbitan monopalmitate), TWEEN 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, PLURONIC® polyls, other block copolymers, and chelators such as EDTA and EGTA can optionally be added to the pharmaceutical compositions to reduce aggregation. These additives are particularly useful if a pump or plastic container is used to administer the pharmaceutical composition. The presence of pharmaceutically acceptable surfactant mitigates the propensity for the composition to aggregate.

The composition of the invention also can contain the preservatives methylparaben (also known as 4-hydroxybenzoic acid methyl ester; methyl p-hydroxybenzoate; or METHYL CHEMOSEPT), ethylparaben (also known as 4-hydroxybenzoic acid ethyl ester; ethyl p-hydroxybenzoate; or ETHYL PARASEPT), propylparaben (also known as 4-hydroxybenzoic acid propyl ester; propyl p-hydroxybenzoate; NIPASOL; or PROPYL CHEMOSEPT) and/or butylparaben (also known as 4-hydroxybenzoic acid propyl ester; propyl p-hydroxybenzoate; or BUTYL CHEMOSEPT). In some aspects, the composition contains methylparaben and/or propylparaben.

The compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the present invention, stabilizers, preservatives, excipients, and the like. The preferred lipids are the phospholipids and the phosphatidyl cholines (lecithins), both natural and synthetic. Methods to form liposomes are known in the art (see Prescott, ed., METH. CELL BIOL. 14:33 (1976)). Liposomes, methods of making and methods of use are described in U.S. Pat. No. 4,089,8091 (process for the preparation of liposomes), U.S. Pat. No. 4,233,871 (methods regarding biologically active materials in lipid vescicles), U.S. Pat. No. 4,438,052 (process for producing mixed miscelles), U.S. Pat. No. 4,485,054 (large multilamellar vescisles), U.S. Pat. No. 4,532,089 (giant-sized liposomes and methods thereof), U.S. Pat. No. 4,897,269 (liposomal drug delivery system), U.S. Pat. No. 5,820,880 (liposomal formulations), and so forth.

During any of the processes for preparation of the compounds of the present invention, it may be necessary and/or desirable to protect sensitive or reactive groups on any of the molecules concerned. This may be achieved by means of conventional protecting groups, such as those described in PROTECTIVE GROUPS IN ORGANIC CHEMISTRY (1973); and GREENE AND WUTS, PROTECTIVE GROUPS IN ORGANIC SYNTHESIS (1991). The protecting groups may be removed at a convenient subsequent stage using methods known from the art.

The compound of the invention can be solubilized or suspended in a preconcentrate (before dilutions with a diluent), added to the preconcentrate prior to dilution, added to the diluted preconcentrate, or added to a diluent prior to mixing with the preconcentrate. The compound of the invention can also be co-administered as part of an independent dosage form, for therapeutic effect. Optionally, the compound of the invention can be present in a first, solubilized amount, and a second, non-solubilized (suspended) amount.

The pharmaceutical formulation can also contain suitable pharmaceutically acceptable carriers comprising excipients and auxiliaries that facilitate processing of the active compounds into preparations that can be administered to animals, as described herein.

For oral administration in the form of a tablet or capsule, a compound may be combined with an oral, non-toxic pharmaceutically acceptable inert carrier such as ethanol, glycerol, water and the like. Moreover, when desired or necessary, suitable binders, lubricants, disintegrating agents, and coloring agents may also be incorporated into the mixture. Suitable binders include, without limitation, starch; gelatin; natural sugars such as glucose or beta-lactose; corn sweeteners; natural and synthetic gums such as acacia, tragacanth, or sodium alginate, carboxymethylcellulose; polyethylene glycol; waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For oral administration, the composition also optionally contains a sweetener. Sweeteners include but are not limited to sucrose, fructose, sodium saccharin, sucralose (SPLENDA®), sorbitol, mannitol, aspartame, sodium cyclamate, and the like and combinations thereof.

The aqueous suspensions, emulsions and/or elixirs for oral administration of this invention can be combined with various sweetening agents, flavoring agents, such as, but not limited to orange or lemon flavors, coloring agents, such as dye stuffs, natural coloring agents or pigments, in addition to the diluents such as water, glycerin and various combinations, as described herein.

The pharmaceutical compositions of the present invention suitable for oral administration may be presented as discrete units such as capsules, dragees, cachets or tablets each containing a predetermined amount of the compound; as a powder or granules; as a solution or a suspension in an aqueous liquid or a non-aqueous liquid; or as an oil-in-water liquid emulsion or a water-in-oil emulsion, and as a bolus, etc.

A tablet may be made by compression or molding, optionally with one or more accessory ingredients. Compressed tablets may be prepared by compressing, in a suitable machine, the compound in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the compound therein.

In addition, the compositions comprising compounds may be incorporated into biodegradable polymers allowing for sustained release of the compound. The biodegradable polymers and their uses are described in detail in Brem et al., 74 J. NEUROSURG. 441-46 (1991). Suitable examples of sustained-release compositions include semipermeable matrices of solid hydrophobic polymers containing a compound of the present invention, which matrices are in the form of shaped articles, e.g., films, or microcapsules. Examples of sustained-release matrices include polyesters, hydrogels (including poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT® (Tap Pharmaceuticals, Inc., Chicago, Ill.) (injectable microspheres composed of lactic acid glycolic acid copolymer and leuprolide acetate), and poly-D-(-)-3-hydroxybutyric acid.

Pharmaceutical compositions suitable for parenteral administration include aqueous and non-aqueous sterile injection solutions which may contain anti-oxidants, buffers, bacteriostats and solutes that render the formulation isotonic with the blood of the intended recipient; and aqueous and non-aqueous sterile suspensions which may include suspending agents and thickening agents. The compositions may be presented in unit-dose or multi-dose containers, sealed ampules and vials, and may be stored in a freeze-dried (lyophilized) condition requiring only the addition of the sterile liquid carrier, water for injections, immediately prior to use. Extemporaneous injection solutions and suspensions may be prepared from sterile powders, granules and tablets of the kind previously described.

For parenteral administration, sterile suspensions and solutions are desired. Isotonic preparations which generally contain suitable preservatives are employed when intravenous administration is desired. The pharmaceutical compositions may be administered parenterally via injection of a pharmaceutical composition comprising a compound dissolved in an inert liquid carrier. The term "parenteral," as used herein, includes, but is not limited to, subcutaneous injections, intravenous, intramuscular, intraperitoneal injections, or infusion techniques. Acceptable liquid carriers include, vegetable oils such as peanut oil, cotton seed oil, sesame oil and the like, as well as organic solvents such as solketal, glycerol formal and the like. The pharmaceutical compositions may be prepared by dissolving or suspending the compound in the liquid carrier such that the final formulation contains from about 0.005% to 30% by weight of a compound.

The composition of the invention can also include additional therapeutic agents such as, but not limited to hydrophilic drugs, hydrophobic drugs, hydrophilic macromolecules, cytokines, peptidomimetics, peptides, proteins, toxoids, sera, antibodies, vaccines, nucleosides, nucleotides, nucleoside analogs, genetic materials and/or combinations thereof.

Examples of therapeutic agents that can be used in the pharmaceutical compositions of the present invention include, but are not limited to, other antineoplastic agents, analgesics and anti-inflammatory agents, anti-anginal agents, antihelmintics, anti arrhythmic agents, anti-arthritic agents, anti-asthma agents, anti-bacterial agents, anti-viral agents, antibiotics, anti-coagulants, anti-depressants, anti-diabetic agents, anti-epileptic agents, anti-emetics, anti-fungal agents, anti-gout agents, anti-hypertensive agents, anti-malarial agents, antimigraine agents, anti-muscarinic agents, anti-parkinson's agents, anti-protozoal agents, anti-thyroid agents, thyroid therapeutic agents, anti-tussives, anxiolytic agents, hypnotic agents, neuroleptic agents, β-blockers, cardiac inotropic agents, corticosteroids, diuretics, gastrointestinal agents, histamine H-receptors antagonists, immunosuppressants, keratolytics, lipid regulating agents, muscle relaxants, nutritional agents, cytokines, peptidomimetics, peptides, proteins, toxoids, sera, sedatives, sex hormones, sex hormone antagonists or agonists, stimulants antibodies, vaccines, nucleosides, nucleoside analogs and genetic materials. Amphiphilic therapeutic agents and nutritional agents can also be included.

The additional therapeutic agent can be solubilized or suspended in a preconcentrate (before dilutions with a diluent), added to the preconcentrate prior to dilution, added to the diluted preconcentrate, or added to a diluent prior to mixing with the preconcentrate. The additional therapeutic agent can also be co-administered as part of an independent dosage form, for therapeutic effect. Optionally, the additional therapeutic agent(s) can be present in a first, solubilized amount, and a second, non-solubilized (suspended) amount. Such additional therapeutic agent(s) can be any agent(s) having therapeutic or other value when administered to an animal, particularly to a mammal, such as drugs, nutrients, and diagnostic agents.

In addition to the compound and compositions of the invention, and additional pharmaceutically active agents, the pharmaceutical formulation can also contain suitable pharmaceutically acceptable carriers comprising excipients and auxiliaries that facilitate processing of the active compounds into preparations that can be administered to animals, as described herein.

Pharmaceutical formulations useful in the present invention can contain a quantity of a compound(s) according to this invention in an amount effective to treat the condition, disorder or disease of the subject being treated.

The invention is also directed to a kit form useful for administration to patients in need thereof. The kit may have a carrier means being compartmentalized in close confinement to receive two or more container means therein, having a first container means containing a therapeutically effective amount of a pharmaceutical composition of the invention and a carrier, excipient or diluent. Optionally, the kit can have additional container mean(s) comprising a therapeutically effective amount of additional agents.

The kit comprises a container for the separate compositions such as a divided bottle or a divided foil packet, however, the separate compositions can also be contained within a single, undivided container. Typically, the kit contains directions for administration of the separate components. The kit form is particularly advantageous when the separate components are preferably administered at different dosage intervals, or when titration of the individual components of the combination is desired by the prescribing physician. The kits of the invention include testing and screening kits and methods, to enable practitioners to measure levels of the active ingredients in bodily fluids. The kits of the invention also include research-grade reagents and kits available for use and purchase by research entities.

IV. Routes of Administration of Compositions Comprising the Compounds of the Invention The invention further relates to the administration of at least one compound disclosed herein by the following routes, including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarenal, intraretinal, intraspinal, intrasynovial, intrathoracic, intrauterine, intravesical, bolus, vaginal, rectal, buccal, sublingual, intranasal, iontophoretic means, or transdermal means.

It can be sometimes desirable to deliver the compounds of the present invention to the subject over prolonged periods of time, for periods of one week to one year from a single administration. Certain medical devices may be employed to provide a continuous intermittent or on demand dosing of a patient. The devices may be a pump of diffusion apparatus, or other device containing a reservoir of drug and optionally diagnostic or monitoring components to regulate the delivery of the drug. Various slow-release, depot or implant dosage forms can be utilized. A dosage form can contain a pharmaceutically acceptable non-toxic salt of a compound disclosed herein that has a low degree of solubility in body fluids, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g., a zinc tannate salt. Additionally, the compounds of the present invention or a relatively insoluble salt such as those just described, can be formulated in a gel, an aluminum monostearate gel with, e.g., sesame oil, suitable for injection. Salts include, but are not limited to, zinc salts, zinc tannate salts, pamoate salts, and the like. Another type of slow-release depot formulation for injection would contain the compound or salt dispersed or encapsulated in a slow degrading, non-toxic, non-antigenic polymer such as a polylactic acid/polyglycolic acid polymer, including the formulations as described in U.S. Pat. No. 3,773,919. The compounds or relatively insoluble salts thereof such as those described above can also be formulated in cholesterol matrix silastic pellets, particularly for use in animals. Additional slow-release, depot or implant formulations, e.g., gas or liquid liposomes are known in the literature. See, e.g., U.S. Pat. No. 5,770,222; SUSTAINED AND CONTROLLED RELEASE DRUG DELIVERY SYSTEMS (1978).

Other examples include provision of the compounds of the present invention to be administered by sustained release delivery system containing a biodegradable composition. The biodegradable composition may be composed of a biodegradable, water-coagulable, non-polymeric material and a biocompatible, non-toxic organic solvent that is miscible to dispersible in an aqueous medium. The delivery system may be implanted at an implant site causing the solvent to dissipate, disperse or leach from the composition into surrounding tissue fluid through a resulting microporous matrix.

The term "implant site" is meant to include a site, in or on which the non-polymeric composition is applied. Implantation or implant site can also include the incorporation of the pharmaceutical composition comprising at least one compound of the present invention with a solid device. The pharmaceutical composition can be incorporated into a coating on a stent that is implanted into a subject. Additionally, other solid or biodegradeable materials can be used as a substrate on which the pharmaceutical composition is applied. The coated material, comprising the pharmaceutical composition is then implanted, inserted or is adjacent to the subject or patient. The term "biodegradable" means that the non-polymeric material and/or matrix of the implant will degrade over time by the action of enzymes, by simple or enzymatically catalyzed hydrolytic action and/or by other similar mechanisms in the human body. By "bioerodible," it is meant that the implant matrix will erode or degrade over time due, at least in part, to contact with substances found in the surrounding tissue fluids, cellular action, and the like. By "bioabsorbable," it is meant that the non-polymeric matrix will be broken down and absorbed within the human body, by a cell, a tissue, and the like.

Non-polymeric materials that can be used in the composition generally are those that are biocompatible, substantially insoluble in water and body fluids, and biodegradable and/or bioerodible. The non-polymeric material is capable of being at least partially solubilized in a water-soluble organic solvent. The non-polymeric materials are also capable of coagulating or solidifying to form a solid implant matrix. The non-polymeric material is combined with a compatible and suitable organic solvent to form a composition that has the desired consistency ranging from watery to viscous to a spreadable putty or paste.

Suitable organic solvents are those that are biocompatible, pharmaceutically-acceptable, and will at least partially dissolve the non-polymeric material. The organic solvent has a solubility in water ranging from miscible to dispersible. Optionally, a pore-forming agent can be included in the composition to generate additional pores in the implant matrix. The pore-forming agent can be any organic or inorganic, pharmaceutically-acceptable substance that is substantially soluble in water or body fluid, and will dissipate from the coagulating non-polymeric material and/or the solid matrix of the implant into surrounding body fluid at the implant site.

The compounds of the present invention are capable of providing a local or systemic biological, physiological or therapeutic effect in the body of an animal. In formulating some pharmaceutical compositions described herein, the compound is preferably soluble or dispersible in the non-polymeric composition to form a homogeneous mixture, and upon implantation, becomes incorporated into the implant matrix. As the solid matrix degrades over time, the compound is capable of being released from the matrix into the adjacent tissue fluid, and to the pertinent body tissue or organ, either adjacent to or distant from the implant site, preferably at a controlled rate. The release of the compound from the matrix may be varied by the solubility of the compound in an aqueous medium, the distribution of the compound within the matrix, the size, shape, porosity, and solubility and biodegradability of the solid matrix. See e.g., U.S. Pat. No. 5,888,533. The amounts and concentrations of ingredients in the composition administered to the patient will generally be effective to accomplish the task intended.

In other aspects, the compounds of the present invention may be administered by bioactive agent delivery systems containing microparticles suspended in a polymer matrix. The microparticles may be microcapsules, microspheres or nanospheres currently known in the art. The microparticles should be capable of being entrained intact within a polymer that is or becomes a gel once inside a biological environment. The microparticles can be biodegradable or non-biodegradable. Many microencapsulation techniques used to incorporate a bioactive agent into a microparticle carrier are taught in the art. See e.g., U.S. Pat. Nos. 4,652,441; 5,100,669; 4,438,253; and 5,665,428.

A preferred polymeric matrix will be biodegradable and exhibit water solubility at low temperature and will undergo reversible thermal gelation at physiological mammalian body temperatures. The polymeric matrix is capable of releasing the substance entrained within its matrix over time and in a controlled manner. The polymers are gradually degraded by enzymatic or non-enzymatic hydrolysis in aqueous or physiological environments. See e.g., U.S. Pat. No. 6,287,588.

Methods of Preparation

Methods of preparing various pharmaceutical compositions with a certain amount of active ingredients are known, or will be apparent in light of this disclosure, to those skilled in the art. Methods of preparing said pharmaceutical compositions can incorporate other suitable pharmaceutical excipients and their formulations as described in REMINGTON'S PHARMACEUTICAL SCIENCES, Martin, E. W., ed., Mack Publishing Company, 19th ed. (1995).

Pharmaceutical preparations of the present invention are manufactured in a manner that is known, including conventional mixing, dissolving, or lyophilizing processes. Thus, liquid pharmaceutical preparations can be obtained by combining the active compounds with solid excipients, optionally grinding the resulting mixture and processing the mixture of granules, after adding suitable auxiliaries, if desired or necessary.

One of ordinary skill in the art will appreciate that a method of administering pharmaceutically effective amounts of the compositions of the invention to a patient in need thereof, can be determined empirically, or by standards currently recognized in the medical arts. The agents can be administered to a patient as pharmaceutical compositions in combination with one or more pharmaceutically acceptable excipients. It will be understood that, when administered to a human patient, the total daily usage of the agents of the compositions of the present invention will be decided within the scope of sound medical judgment by the attending physician. The specific therapeutically effective dose level for any particular patient will depend upon a variety of factors: the type and degree of the cellular response to be achieved; activity of the specific agent or composition employed; the specific agents or composition employed; the age, body weight, general health, gender and diet of the patient; the time of administration, route of administration, and rate of excretion of the agent; the duration of the treatment; drugs used in combination or coincidental with the specific agent; and like factors well known in the medical arts. It is well within the skill of the art to start doses of the agents at levels lower than those required to achieve the desired therapeutic effect and to gradually increase the dosages until the desired effect is achieved.

Dosaging can also be administered in a patient-specific manner to provide a predetermined concentration of the agents in the blood, as determined by techniques accepted and routine in the art.

V. Dosage Determinations

In general, the compounds disclosed herein may be used alone or in concert with other therapeutic agents at appropriate dosages defined by routine testing in order to obtain optimal efficacy while minimizing any potential toxicity. The dosage regimen utilizing a compound of the present invention may be selected in accordance with a variety of factors including type, species, age, weight, sex, medical condition of the patient; the severity of the condition to be treated; the route of administration; the renal and hepatic function of the patient; and the particular compound employed. A physician or veterinarian of ordinary skill can readily determine and prescribe the effective amount of the drug required to prevent, counter, or arrest the progress of the condition.

Optimal precision in achieving concentrations of drug within the range that yields maximum efficacy with minimal toxicity may require a regimen based on the kinetics of the compound's availability to one or more target sites. Distribution, equilibrium, and elimination of a drug may be considered when determining the optimal concentration for a treatment regimen. The dosages of a compound disclosed herein may be adjusted when combined to achieve desired effects. On the other hand, dosages of these various therapeutic agents may be independently optimized and combined to achieve a synergistic result wherein the pathology is reduced more than it would be if either agent were used alone.

In particular, toxicity and therapeutic efficacy of a compound disclosed herein may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effect is the therapeutic index and it may be expressed as the ratio $LD_{50}/ED_{50}$. Compounds exhibiting large therapeutic indices are preferred except when cytotoxicity of the compound is the activity or therapeutic outcome that is desired. Although compounds that exhibit toxic side effects may be used, a delivery system can target such compounds to the site of affected tissue in order to minimize potential damage to uninfected cells and, thereby, reduce side effects. Generally, the compounds of the present invention may be administered in a manner that maximizes efficacy and minimizes toxicity.

Data obtained from cell culture assays and animal studies may be used in formulating a range of dosages for use in humans. The dosages of such compounds lies preferably within a range of circulating concentrations that include the $ED_{50}$ with little or no toxicity. The dosage may vary within this range depending upon the dosage form employed and the route of administration utilized. For any compound used in the methods of the present invention, the therapeutically effective dose may be estimated initially from cell culture assays. A dose may be formulated in animal models to achieve a circulating plasma concentration range that includes the $IC_{50}$ (the concentration of the test compound that achieves a half-maximal inhibition of symptoms) as determined in cell culture. Such information may be used to accurately determine useful doses in humans. Levels in plasma may be measured, by high performance liquid chromatography.

Moreover, the dosage administration of the pharmaceutical compositions of the present invention may be optimized using a pharmacokinetic/pharmacodynamic modeling system. One or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See U.S. Pat. No. 6,747,002, which is entirely expressly incorporated herein by reference.

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount," as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that inhibits in a subject the onset or progression of a disorder as being sought by a researcher, veterinarian, medical doctor or other clinician. Thus, the present invention further provides combinations of two or more therapeutic agents wherein, (a) each therapeutic agent is administered in an independently therapeutically or prophylactically effective amount; (b) at least one therapeutic agent in the combination is administered in an amount that is sub-therapeutic or subprophylactic if administered alone, but is therapeutic or prophylactic when administered in combination with the second or additional therapeutic agents according to the invention; or (c) both therapeutic agents are administered in an amount that is subtherapeutic or sub-prophylactic if administered alone, but are therapeutic or prophylactic when administered together. Combinations of three or more therapeutic agents are analogously possible. Methods of combination therapy include co-administration of a single formulation containing all active agents; essentially contemporaneous administration of more than one formulation; and administration of two or more active agents separately formulated.

More specifically, the pharmaceutical compositions may be administered in a single daily dose, or the total daily dosage may be administered in divided doses of two, three, or four times daily. Doses may be administered for one week, one month, or over the course of several months, 3, 6, 9 or 12 months, or intervals known in the art and determined to be clinically relevant. Doses may be continued throughout the life of the patient, or discontinues when clinical judgment warrants. The daily dosage of the compositions may be varied over a wide range from about 0.0001 to about 1,000 mg per patient, per day. The range may more particularly be from about 0.001 mg/kg to 10 mg/kg of body weight per day, about 0.1-100 mg, about 1.0-50 mg or about 1.0-20 mg per day for adults (at about 60 kg). Additionally, the dosages may be about 0.5-10 mg/kg per day, about 1.0-5.0 mg/kg per day, 5.0-10 mg/kg per day, or equivalent doses as determine by a practitioner, to achieve a serum concentration that is clinically relevant.

In the case of injections, it is usually convenient to give by an intravenous route in an amount of about 0.01-30 mg, about 0.1-20 mg or about 0.1-10 mg per day to adults (at about 60 kg). Intravenous doses may include a bolus or a slow dosing. In the case of other animals, the dose calculated for 60 kg may be administered as well.

As a non-limiting example, treatment of humans or animals can be provided as a one-time or periodic dosage of a compound of the present invention 0.0001 to about 1,000 mg per patient, per day. The range may more particularly be from about 0.001 mg/kg to 10 mg/kg of body weight per day, about 0.1-100 mg, about 1.0-50 mg or about 1.0-20 mg per day for adults (at about 60 kg). Additionally, the dosages may be about 0.5-10 mg/kg per day, about 1.0-5.0 mg/kg per day, 5.0-10 mg/kg per day, or equivalent doses as determine by a practitioner, to achieve a serum concentration that is clinically relevant.

Specifically, the pharmaceutical compositions of the present invention may be administered at least once a week over the course of several weeks. In one aspect, the pharmaceutical compositions are administered at least once a week over several weeks to several months. In another aspect, the pharmaceutical compositions are administered once a week over four to eight weeks. In yet another aspect, the pharmaceutical compositions are administered once a week over four weeks.

VI. Methods of Use of the Compounds of the Invention

In another aspect, the present invention is further directed to methods that have utility in the treatment of any diseases associated with neuron loss. More specifically, the present invention further provides methods for stimulating neurogenesis and/or inhibiting neuronal degeneration in a mammal. In a specific aspect, the method may comprise administering to a mammal a composition comprising a compound described herein. The composition comprising a compound described herein may be administered in an amount effective to stimulate neurogenesis and/or inhibit neuronal degeneration in the mammal.

In a further aspect, a method for treating a mammal afflicted with a neurodegenerative disease or condition may comprise administering an effective amount of a composition comprising a compound described herein to the mammal. In other aspects, the neurodegenerative disease or condition may be selected from the group consisting of ischemic stroke, traumatic brain injury, acute disseminated encephalomyelitis, amyotrophic lateral sclerosis (ALS), retinitis pigmentosa, mild cognitive impairment, Alzheimer's disease, Pick's disease, senile dementia, progressive supranuclear palsy, subcortical dementias, Wilson disease, multiple infarct disease, arteriosclerotic dementia, AIDS associated dementia, cerebellar degeneration, spinocerebellar degeneration syndromes, Friedreichs ataxia, ataxia telangiectasia, epilepsy-related brain damage, spinal cord injury, restless legs syndrome, Huntington's disease, Parkinson's disease, striatonigral degeneration, cerebral vasculitis, mitochondrial encephalomyopathies, neuronal ceroid lipofuscinosis, spinal muscular atrophies, lysosomal storage disorders with central nervous system involvement, leukodystrophies, urea cycle defect disorders, hepatic encephalopathies, renal encephalopathies, metabolic encephalopathies, porphyria, bacterial meningitis, viral meningitis, meningoencephalitis, prion diseases, poisonings with neurotoxic compounds, Guillain Barre syndrome, chronic inflammatory neuropathies, polymyositis, dermatomyositis and radiation-induced brain damage. Included in the aspect is neurodegeneration including peripheral neuropathy due to therapeutic administration of cranial irradiation or chemotherapeutic agents.

In another aspect, a method for treating a mammal afflicted with a neuropsychiatric disease or condition may comprise administering an effective amount of a composition comprising a compound described herein to the mammal. In other aspects, the neuropsychiatric disease or condition may be selected from the group consisting of anxiety disorders, childhood disorders, eating disorders, mood disorders, cognitive disorders, personality disorders, psychotic disorders, and substance-related disorders.

More specifically, the types of psychiatric diseases/disorders/conditions that may be treated using the compounds of the present invention include anxiety disorders including, but not limited to, acute stress disorder, panic disorder, agoraphobia, social phobia, obsessive-compulsive disorder, posttraumatic stress disorder, and generalized anxiety disorder; childhood disorders including, but not limited to, attention-deficit hyperactivity disorder, asperger's disorder, autistic disorder, conduct disorder, oppositional defiant disorder, separation anxiety disorder, and tourette's disorder; eating disorders including, but not limited to, anorexia nervosa, and bulimia nervosa; mood disorders including, but not limited to, major depressive disorder, bipolar disorder (manic depression), cyclothymic disorder, and dysthymic disorder; cognitive disorders including, but not limited to, delirium, multi-infarct dementia, dementia associated with alcoholism, dementia of the alzheimer type, and dementia; personality disorders including, but not limited to, paranoid personality disorder, schizoid personality disorder, schizotypal personality disorder, antisocial personality disorder, borderline personality disorder, histrionic personality disorder, narcissistic personality disorder, avoidant personality disorder, dependent personality disorder, and obsessive-compulsive personality disorder; psychotic disorders including, but not limited to, schizophrenia, delusional disorder, brief psychotic disorder, schizophreniform disorder, schizoaffective disorder, and shared psychotic disorder; substance-related disorders including, but not limited to, alcohol dependence, amphetamine dependence, cannabis dependence, cocaine dependence, hallucinogen dependence, inhalant dependence, nicotine dependence, opioid dependence, phencyclidine dependence, and sedative dependence.

In another aspect, a method for treating a mammal afflicted with traumatic brain injury may comprise administering an effective amount of a composition comprising a compound described herein to the mammal.

In another aspect, a method for treating a mammal afflicted with traumatic nerve injury may comprise administering an effective amount of a composition comprising a compound described herein to the mammal.

In another aspect, the invention includes a compound having a structure according to Formula I:

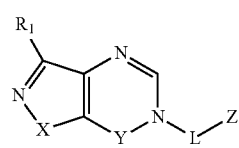

Formula I wherein $R_1$ is hydrogen, alkyl, branched alkyl, aryl, aralalkyl, benzyl, napthyl, cycloalkyl of 1 to 12 carbon atoms, or a heterocycle, when $R_1$ is not hydrogen it can be optionally substituted with H, OH, alkyl, alkoxy, halogen, —$CF_3$, —$R_2$, —$OR_2$, —$SR_2$, —$N(R_2)_2$, —CN, —$NO_2$, —$NCO(O)R_2$, —C(O) $R_2$, —$C(O)N(R_2)_2$, —$S(O)_2R_2$, —$S(O)_2NR_2$, —$S(O)R_2$, —$C(O)R_2$, —$C(O)OR_2$, or —$C(O)N(R_2)_2$ wherein each $R_2$ is independently H, alkyl, alkenyl, alkynyl, aryl, heterocycle, protecting group or prodrug moiety;

L is [$CH_2$]$_{2-6}$, —$CH_2$—(C=O)—$CH_2$—,

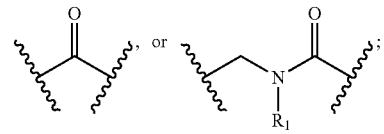

X is S, $SO_2$, O, or NH;
Y is

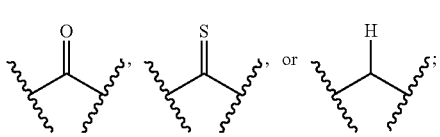

Z is

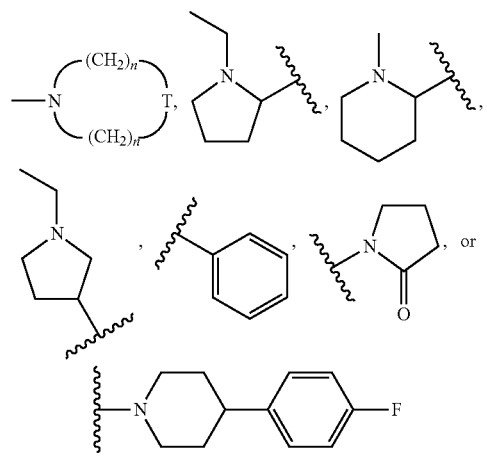

each optionally substituted with H, OH, alkyl, alkoxy, halogen, or —$CF_3$;
T is O, S, or $NR_1$;
n is 2 or 3;
wherein each $R_1$ is independent and may be the same as each other or preferably different.

The invention also includes a method for stimulating neurogenesis and/or inhibiting neuronal degeneration in a mammal, comprising administering a pharmaceutical composition in an amount effective to stimulate neurogenesis and/or inhibit neuronal degeneration in the mammal, said pharmaceutical composition comprising:

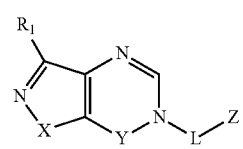

Formula I wherein $R_1$ is hydrogen, alkyl, branched alkyl, aryl, aralalkyl, benzyl, napthyl, cycloalkyl of 1 to 12 carbon atoms, or a heterocycle, when $R_1$ is not hydrogen it can be optionally substituted with H, OH, alkyl, alkoxy, halogen, —CF$_3$, —R$_2$, —OR$_2$, —SR$_2$, —N(R$_2$)$_2$, —CN, —NO$_2$, —NC(O)R$_2$, —C(O) R$_2$, —C(O)N(R$_2$)$_2$, —S(O)$_2$R$_2$, —S(O)$_2$NR$_2$, —S(O)R$_2$, —C(O)R$_2$, —C(O)OR$_2$, or —C(O)N(R$_2$)$_2$ wherein each R$_2$ is independently H, alkyl, alkenyl, alkynyl, aryl, heterocycle, protecting group or prodrug moiety;

L is [CH$_2$]$_{2-6}$, —CH$_2$—(C=O)—CH$_2$—,

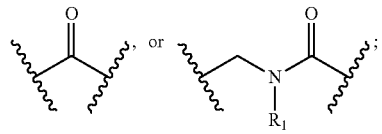

X is S, SO$_2$, O, or NH;
Y is

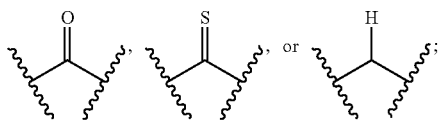

Z is

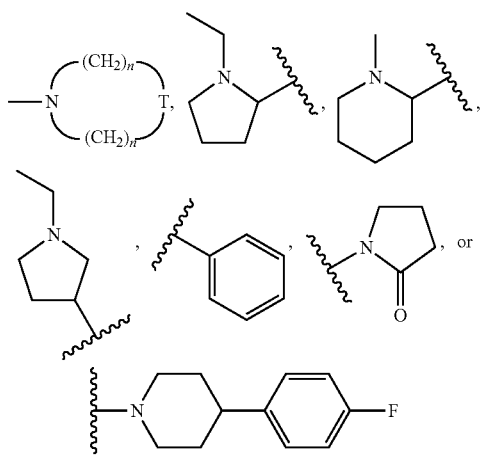

each optionally substituted with H, OH, alkyl, alkoxy, halogen, or —CF$_3$;
T is O, S, or NR$_1$;
n is 2 or 3;
wherein each R$_1$ is independent and may be the same as each other or preferably different a pharmaceutically acceptable carrier; and
optionally wherein the pharmaceutical composition is administered to a patient in need thereof, to treat a condition selected from the group consisting of neurodegenerative disease, psychiatric disorders and aging.

Also included is a method for stimulating neurogenesis and/or inhibiting neuronal degeneration in a mammal, comprising administering a pharmaceutical composition in an amount effective to stimulate neurogenesis and/or inhibit neuronal degeneration in the mammal, additionally including wherein the pharmaceutical composition is administered to a patient in need thereof, to treat a condition selected from the group consisting of neurodegenerative disease, psychiatric disorders and aging, the pharmaceutical compositions comprising a compound selected from the group consisting of:

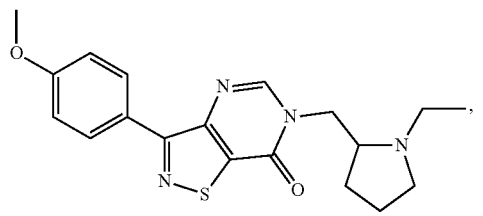

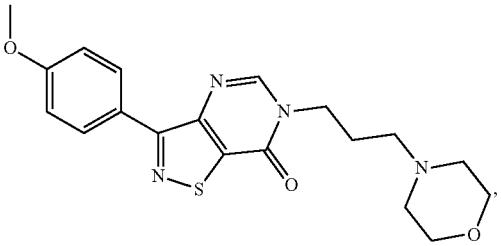

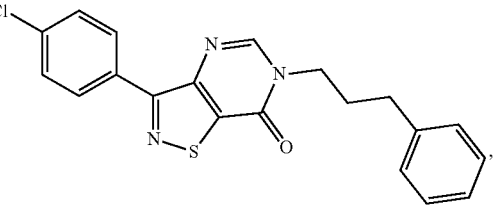

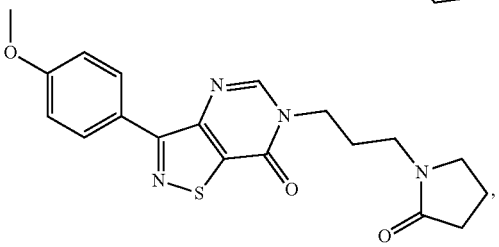

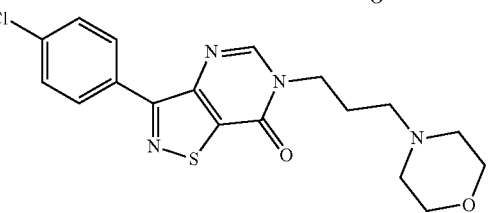

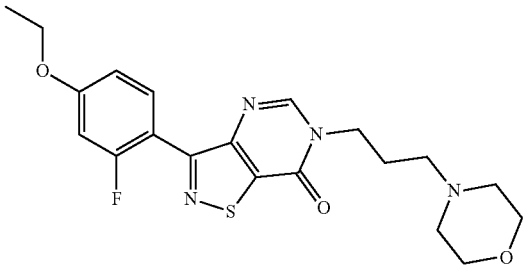

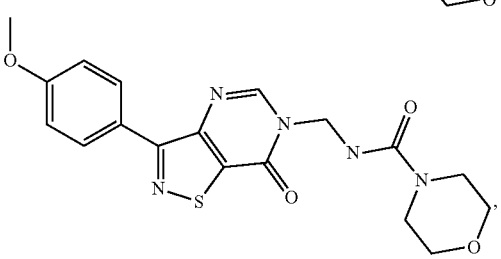

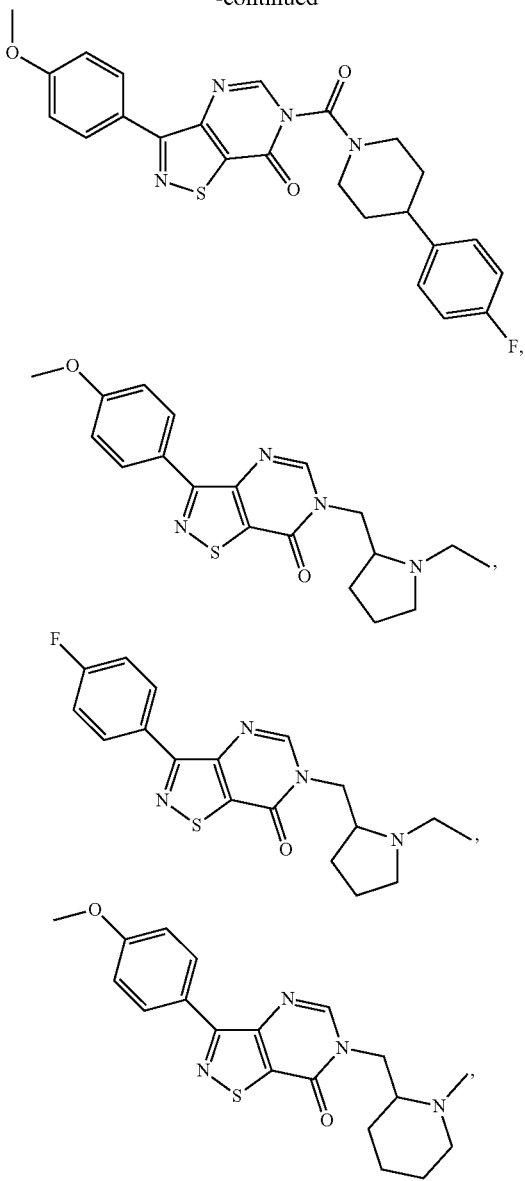

and pharmaceutically acceptable salts, hydrates, or solvates thereof, and a pharmaceutically carrier.

The invention also includes a method wherein the pharmaceutical comprising any one or a combination thereof, of the compositions described herein is administered to a patient in need thereof, to treat a condition including neurodegnerative disease, psychiatric disorders, brain injury, nerve injury and/or aging.

The invention is also directed to methods of stimulating neurogenesis and/or inhibiting neurodegeneration in vitro and ex vivo. Examples of in vitro uses include, but are not limited to, stimulating growth of neurons in cultured cells and tissue, for example, muscle, skin, bone, cartilage, ligament, tendon, tooth, eye, brain, spinal cord, heart, blood vessel, lymph node, ovary, oviduct, uterus, vagina, mammary gland, testicular, seminal vesicle, penis, hypothalamus, pituitary, thyroid, pancreas, adrenal gland, kidney, ureter, bladder, urethra, mouth, esophagus, stomach, small intestine, large intestine, salivary gland, taste bud, nasal, trachea, and lung tissue. Non-limiting examples of ex vivo uses include inhibiting neurodegeneration or stimulating neurogenesis in organ tissues, including but not limited to intact organs and organ systems such as muscle, skin, bone, cartilage, ligament, tendon, tooth, eye, brain, spinal cord, heart, blood vessel, lymph node, ovary, oviduct, uterus, vagina, mammary gland, testicular, seminal vesicle, penis, hypothalamus, pituitary, thyroid, pancreas, adrenal gland, kidney, ureter, bladder, urethra, mouth, esophagus, stomach, small intestine, large intestine, salivary gland, taste bud, nasal, trachea, and lung tissue. In addition, the compositions and methods of the invention are useful in conjunction with pluripotent and multipotent stem cells, including but not limited to adult neural stem cells, which retain the capacity to differentiate into a wide range of neurons and glia. Neurons derived from such neural stem cells are capable of migrating to various regions of the CNS, receiving afferent innervation, forming axonal projections, and expressing neurotransmitters. The compositions of the invention may be used alone to promote neurogenesis of neural stem cells in vitro, in vivo and ex vivo, and may also be advantageously used in combination with known growth factors including, but not limited to fibroblast growth factors (FGFs), epidermal growth factors (EGFs), transforming growth factors (TGFs) and/or neurotrophic factors, non-limited examples of which include brain-derived neurotrophic growth factor (BDNF) and ciliary neurotrophic factor (CNTF). Accordingly, the compositions and methods of the invention are useful in regenerative medicine, in which stem cells are coaxed into forming cells of any lineage (including neural cells) and then delivered to regions of injury or degeneration to treat disease. Use of the compositions and methods of the invention is advantageous in conjunction with growth factors to direct endogenous neural stem cells to differentiate into neurons or glia, as well as in cell-replacement therapies based on delivery of ex vivo-derived neural cells to areas of injury or degeneration.

The invention also includes compounds and compositions wherein the compounds of the invention are present in a salt form. Examples of salts include basic nitrogen-containing bisphosphonic acid salts, ammonium salts, alkali metal salts such as potassium and sodium (including but not limited to mono-, di- and tri-sodium) salts, alkaline earth metal salts such as calcium, magnesium and manganese, salts with organic bases such as dicyclohexylamine salts, N-methyl-D-glucamine, and salts with organic amino acids such as arginine, lysine or histadine. Non-toxic, physiologically acceptable salts are preferred.

The invention also includes a kit comprising two or more containers, having a first container containing a therapeutically effective amount of the pharmaceutical composition comprising any one of Formulas I to XII, and a second container comprising a carrier, excipient or diluent, and/or wherein a third container comprises a therapeutically-acceptable amount of an additional therapeutically active agent. The kit also comprises the composition comprising any one of Formulas I to XII, standardized research grade reagents and control standards and also can comprise two or more compositions comprising a compound of any of Formulas I to XII.

The invention includes a method to promote neurogenesis in a mammalian cell including neural stem cells, embryonic stem cells and progenitor cells, said method comprising: culturing the cells in a cell medium, in the presence of the composition comprising any of Formulas I to XII, and observing said cells for expression of neurogenesis, including greater cell numbers, quality of the cells, differentiation of cells, or a combination thereof.

Other objectives, features and advantages of the present invention will become apparent from the following specific examples. The specific examples, while indicating specific aspects of the invention, are provided by way of illustration only. Accordingly, the present invention also includes those various changes and modifications within the spirit and scope of the invention that may become apparent to those skilled in the art from this detailed description. The invention will be further illustrated by the following non-limiting examples.

EXAMPLES

Example 1

Identification of Compounds

The in vitro neurogenesis test was performed using human neuronal progenitors cells. By way of background, the human neuronal progenitor cells can be cultured in media and have the potential to produce mature functional neurons. The neurogenesis factor in the culture media can promote the number of the progenitor cells which differentiate into neurons. Indeed, it is a widely accepted in vitro model to test a chemical's neurogenetic property.

Cells were obtained as human neuronal progenitors from a commercial source and were grown for up to three passages or at any time differentiated to potentially produce mature functional neurons in culture. Following two passages to expand the cells, progenitors were seeded into multi-well microplates and the media were changed to differentiation media (minus serum and mitogen). Within 2 hrs of this media change, a vehicle, positive control or test compound were added to each well. Also, they were added with every further media change (50% volume change every other day). Control wells contained cells and vehicle (0.2% DMSO in DMEM/F12). Other wells contained positive controls for neuronal progenitor growth, leukemia inhibitory factor (LIF, 10 ng/ml).

The cells were stained using MAP-2, a neuronal marker, on day 11. Then, each test compound was assessed for the ability to promote an increase in neuron number and compared with the positive control, leukemia inhibitory factor (LIF).

The data in Table 2 demonstrates that examples of the compounds of the present invention showed higher neurogenesis activity than the positive control in the in vitro neurogenesis test. That is, the cells given the subject compound showed a further increased number of neurons as compared to the cells given the positive control.

TABLE 2

Effects of compounds on the increase in the neuron numbers compared with the vehicle control

| Compound | % of Control |
|---|---|
| 3-(4-Methoxyphenyl)-6-[(1-ethylpyrrolidin-2-yl)methyl]-isothiazolo[4,5-d]pyrimidin-7(6H)-one | 107 |
| 3-(4-Methoxyphenyl)-6-[3-(4-morpholinyl)propyl]-isothiazolo[4,5-d]pyrimidin-7(6H)-one | 115 |

Example 2

Examination of Compounds Effectiveness to Inhibit Neuronal Degeneration

The effective compounds were then subjected to the in vitro neuron degeneration test. This test as applied for neuroprotective discovery involved the ability of the drugs to inhibit apoptosis and necrosis.

In measuring the ability of inhibiting apoptosis, mature neurons (3-4 weeks following initiation of differentiation) were treated with staurosporine to induce apoptosis. A low concentration of staurosporine (10-100 nM) or beta amyloid 1-42 peptide at 1-10 μM or peptide beta amyloid 25-35 at 10-75 μM concentration was used to stimulate apoptosis. At the same time as treating with staurosporine, the neurons were treated with vehicle or one of the test agents. Because there was strong data demonstrating that staurosporine activated caspase-3 to initiate the apoptotic pathway, the compounds of the invention abilities of inhibiting staurosporine-induced apoptosis were quantified by the amount of activated caspase-3. Each compound's inhibitory ability was compared with vehicle and staurosporine.

Necrosis of the mature neurons was initiated using beta amyloid 1-42 peptide at 1-10 μM or peptide beta amyloid 25-35 at 10-75 μM concentration. This synthetic peptide was of the same length naturally found in AD brain. Because lactate dehydrogenase (LDH) is released from cells when the plasma membrane is impaired, the cell loss was quantified by the amount of LDH released into the media following a 24-48 hr treatment. The ability of neurogenic agents to reduce the LDH release induced by beta amyloid, versus vehicle control was used as the measurement of inhibition of neuron degeneration.

Dysfunctional neurons were initiated using any of the above agents or using hydrogen peroxide at 1-100 μM concentration. Using a dye that measures metabolic activity of the cells, such as MTT or ALAMARBLUE®, we determined the reduction of respiratory capacity of the cells, which indicated neuron dysfunction. The ability of neurogenic agents to inhibit hydrogen peroxide-induced reduction in cellular respiration was used as a measure of inhibition of neuronal dysfunction, a potential step that lead to degeneration.

Then the compounds were subjected to a series of tests to determine the underlining mechanism of their neurogenesis and neuroprotective effectiveness as well as their toxicities. Examples of receptors that were examined in this screen were: adenosine, adrenergic, cannabinoid, dopamine, GABA, glutamate, histamine, muscarinic, opiate receptors as well as calcium, potassium and sodium channels. Then, the compounds were tested in a HERG cellular test to identify their potential cardiac toxicity, an Ames test to identify their mutagenicity, and an Irwin screen to identify their central nervous system toxicity.

The compounds' efficacies were evaluated in the in vivo Behavior Aging Model test and a transgenic models of Alzheimer's test. In the Behavior Aging Model, the compounds were assessed by measuring the ability of producing improvement in cognitive function of motor skills of 21-month-old C57BL/6 mice. The ability of C57BL/6 mice to learn the water maze task has been previously shown to decline with age (e.g., Fordyce and Wehner, 1993; Frick et al., 2000; Forster et al., 1996; Sumien et al., 2004; McDonald & Forster 2005, in press), and is associated with the degree of hippocampal neurogenesis (Kempermann et al., 2002) and with functional indicators of hippocampal synaptic plasticity (van Praag et al., 1999). A series of behavior tests that relate to the learning of an active avoidance response, the measurement of reaction time, the memory for habituation, the age-sensitive measures of motor skills, spontaneous ambulation, and sensory function were carried out to assess the scope and specificity of behavior improvement.

Certain compounds were further analyzed to determine their ability to inhibit neurodegeneration by hydrogen peroxide. Human neurons are treated with hydrogen peroxide (50 uM) for up to 6 hrs and then neuronal loss is measured using Alamar Blue respiration. If either NNI-A (Formula X) or NNI-B (Formula XI) is added along with hydrogen peroxide less loss of respiration is observed. These results are demonstrated in FIG. 1.

Compounds for testing were chosen to have fair blood brain barrier penetration ($Log_{BB} > -0.3$) and also have drug-like properties, i.e., they follow "Lipinki's Rule of Five" (See, C A Lipinski, *Adv. Drug Del. Rev.* 1997, 23, 3). The "Rule of 5" states that: poor absorption or permeation is more likely when:

1. There are more than 5 H-bond donors (expressed as the sum of OHs and NHs).
2. The Molecular Weight is over 500.
3. The $Log_P$ is over 5 (or M Log P is over 4.15).
4. There are more than 10 H-bond acceptors (expressed as the sum of Ns and Os).

Having now fully described this invention, it will be understood to those of ordinary skill in the art that the same can be performed within a wide and equivalent range of conditions, formulations and other parameters without affecting the scope of the invention or any aspect thereof. All patents and publications cited herein are fully incorporated by reference in their entirety.

The invention claimed is:

1. A compound having a structure:

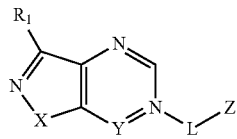

wherein $R_1$ is aryl, optionally substituted with H, OH, alkyl, alkoxy, or halogen;
L is $[CH_2]_{1-6}$;
X is S, $SO_2$, O, or NH;
Y is

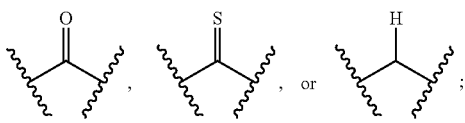

Z is

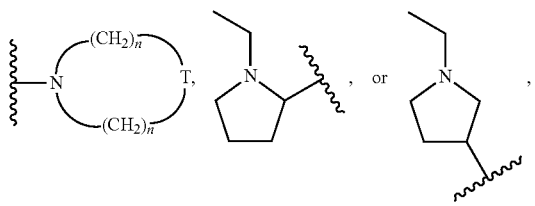

each optionally substituted with H, OH, alkyl, alkoxy, halogen, or $-CF_3$;
T is O, S, or $NR_1$;
n is 2 or 3;
wherein each $R_1$ is independent and may be the same as each other or preferably different.

2. A method for stimulating neurogenesis and/or inhibiting neuronal degeneration in a mammal, comprising administering a pharmaceutical composition in an amount effective to stimulate neurogenesis and/or inhibiting neuronal degeneration in the mammal, said pharmaceutical composition comprising a compound of claim 1 or pharmaceutically acceptable salts, hydrates or solvates thereof, and a pharmaceutically acceptable excipient or carrier.

3. The method of claim 2, wherein the mammal is human.

4. The method of claim 3, wherein the human is a patient suffering from a condition selected from the group consisting of neurodegenerative disease, brain injury, nerve injury, psychiatric disorders and aging.

* * * * *